(12) United States Patent
Cortez, Jr. et al.

(10) Patent No.: US 10,512,748 B2
(45) Date of Patent: Dec. 24, 2019

(54) HEATED NEBULIZER ADAPTER FOR RESPIRATORY THERAPY

(71) Applicant: Vapotherm, Inc., Exeter, NH (US)

(72) Inventors: Felino V. Cortez, Jr., Bowie, MD (US); Charles Busey, Grasonville, MD (US); George C. Dungan, II, Dallas, TX (US)

(73) Assignee: VAPOTHERM, INC., Exeter, NH (US)

( * ) Notice: Subject to any disclaimer, the term of this patent is extended or adjusted under 35 U.S.C. 154(b) by 1177 days.

(21) Appl. No.: 14/733,180

(22) Filed: Jun. 8, 2015

(65) Prior Publication Data

US 2015/0352299 A1 Dec. 10, 2015

Related U.S. Application Data

(60) Provisional application No. 62/008,880, filed on Jun. 6, 2014.

(51) Int. Cl.
*A61M 16/16* (2006.01)
*A61M 11/02* (2006.01)
(Continued)

(52) U.S. Cl.
CPC ............ *A61M 16/16* (2013.01); *A61M 11/02* (2013.01); *A61M 11/06* (2013.01); *A61M 11/04* (2013.01);
(Continued)

(58) Field of Classification Search
CPC .... A61M 11/00; A61M 11/04; A61M 11/041; A61M 11/06; A61M 11/02;
(Continued)

(56) References Cited

U.S. PATENT DOCUMENTS 2,485,184 A 10/1949 Blackman et al.
3,826,255 A * 7/1974 Havstad ................. A61M 11/06
128/200.18
(Continued)

FOREIGN PATENT DOCUMENTS

EP 1317941 6/2003
JP 2003250894 9/2003
(Continued)

OTHER PUBLICATIONS

International Search Report and Written Opinion for PCT/2013/022692 dated Jul. 29, 2014.
(Continued)

*Primary Examiner* — Colin W Stuart
(74) *Attorney, Agent, or Firm* — White & Case LLP

(57) ABSTRACT

Systems, methods, and devices are described for heating nebulizer adapters. In certain embodiments, a nebulizer adapter includes a cup having an interior wall defining a gas mixing chamber, an exterior wall, and a fluid cavity disposed between the interior wall and the exterior wall. The nebulizer adapter also includes an inlet port having a fluid lumen in fluid communication with the fluid cavity and a breathing gas inlet lumen in fluid communication with the mixing chamber. The nebulizer adapter further includes an outlet having a breathing gas outlet lumen, and a drain port in fluid communication with the mixing chamber and having a drain lumen that passes from the interior wall to the exterior wall of the cup.

32 Claims, 7 Drawing Sheets

(51) Int. Cl.
*A61M 11/06* (2006.01)
*A61M 11/04* (2006.01)
*A61M 16/10* (2006.01)
*A61M 16/08* (2006.01)
*A61M 16/06* (2006.01)
*A61M 39/10* (2006.01)

(52) U.S. Cl.
CPC ....... *A61M 11/041* (2013.01); *A61M 16/0672* (2014.02); *A61M 16/0808* (2013.01); *A61M 16/0816* (2013.01); *A61M 16/1095* (2014.02); *A61M 39/105* (2013.01); *A61M 2039/1072* (2013.01); *A61M 2205/36* (2013.01)

(58) Field of Classification Search
CPC .. A61M 11/006; A61M 11/005; A61M 16/00; A61M 16/08; A61M 16/0808; A61M 16/0816; A61M 16/0875; A61M 16/0833; A61M 16/0883; A61M 16/16; A61M 16/18; A61M 39/00; A61M 39/10; A61M 39/105; A61M 2039/0036; A61M 2039/1072; A61M 2039/1077; A61M 2205/36; A61M 2205/366
See application file for complete search history.

(56) References Cited

U.S. PATENT DOCUMENTS

| | | | |
|---|---|---|---|
| 3,864,326 A | | 2/1975 | Babington |
| 3,945,378 A | | 3/1976 | Paluch |
| 4,177,945 A | | 12/1979 | Schwartz et al. |
| 4,805,609 A | | 2/1989 | Roberts et al. |
| 4,819,625 A | | 4/1989 | Howe |
| 4,832,012 A | | 5/1989 | Raabe et al. |
| 4,911,157 A | | 3/1990 | Miller |
| 4,915,105 A | | 4/1990 | Lee |
| 4,951,661 A | * | 8/1990 | Sladek .............. A61M 16/0808 128/202.27 |
| 5,099,833 A | * | 3/1992 | Michaels .............. A61M 16/08 128/200.14 |
| 5,226,411 A | | 7/1993 | Levine |
| 5,335,656 A | | 8/1994 | Bowe et al. |
| 5,461,695 A | | 10/1995 | Knoch |
| 5,584,285 A | | 12/1996 | Salter et al. |
| 5,630,409 A | | 5/1997 | Bono et al. |
| 6,328,030 B1 | * | 12/2001 | Kidwell .................. A61M 11/06 128/200.14 |
| 8,561,607 B2 | | 10/2013 | Cortez, Jr. et al. |
| 9,333,317 B2 | | 5/2016 | Cortez, Jr. et al. |
| 2002/0053346 A1 | | 5/2002 | Curti et al. |
| 2003/0150445 A1 | * | 8/2003 | Power .............. A61M 15/0085 128/200.14 |
| 2004/0011364 A1 | | 1/2004 | Dhuper et al. |
| 2004/0221846 A1 | | 11/2004 | Curti et al. |
| 2004/0237178 A1 | | 12/2004 | Landeros |
| 2005/0217667 A1 | | 10/2005 | Dhuper et al. |
| 2005/0229926 A1 | | 10/2005 | Fink et al. |
| 2005/0229927 A1 | | 10/2005 | Fink et al. |
| 2005/0229928 A1 | | 10/2005 | Ivri et al. |
| 2005/0229929 A1 | | 10/2005 | Ivri |
| 2005/0252509 A1 | * | 11/2005 | Rustad .................. A61M 16/08 128/203.12 |
| 2006/0078506 A1 | | 4/2006 | Niven et al. |
| 2008/0000470 A1 | | 1/2008 | Minocchieri et al. |
| 2009/0241948 A1 | | 10/2009 | Clancy et al. |
| 2010/0089395 A1 | | 4/2010 | Power et al. |
| 2010/0258114 A1 | | 10/2010 | Cortez, Jr. et al. |
| 2011/0000487 A1 | | 1/2011 | Moa et al. |
| 2011/0073116 A1 | | 3/2011 | Genger et al. |
| 2013/0000641 A1 | | 1/2013 | Mazela et al. |
| 2013/0074842 A1 | * | 3/2013 | Boucher ................ A61M 16/16 128/203.16 |
| 2013/0255670 A1 | | 10/2013 | Ott et al. |
| 2014/0109899 A1 | * | 4/2014 | Boucher ................ A61M 11/06 128/200.18 |

FOREIGN PATENT DOCUMENTS

| | | |
|---|---|---|
| JP | 2007537833 | 12/2007 |
| RU | 2009111135 | 10/2010 |
| RU | 2432190 | 10/2011 |
| WO | WO-1989009565 | 10/1989 |
| WO | WO-2002/004054 | 1/2002 |
| WO | WO-2003035141 | 5/2003 |
| WO | WO-2005/115520 A1 | 12/2005 |
| WO | WO-2009078805 | 6/2009 |
| WO | WO-2009149336 | 12/2009 |
| WO | WO-2010/035251 A2 | 4/2010 |
| WO | WO-2010/091259 A2 | 8/2010 |
| WO | WO-2012020004 | 2/2012 |

OTHER PUBLICATIONS

International Search Report and Written Opinion for PCT/2010/023331 dated Oct. 19, 2010.
Supplementary European Search Report for EP13740914.0 dated Jul. 8, 2015.
International Search Report and Written Opinion for PCT/US2015/034663 dated Aug. 20, 2015.
Cairo, "Mosby's Respiratory Care Equipment," 9th Ed. pp. 20, 98 (2014) (4 pages).
Kacmarek et al, "Egan's Fundamentals of Respiratory Care," Physical Principles of Respiratory Care, Chap. 6, 11th Ed., pp. 123-124 (2017) (5 pages).
Sacci, R., "Air entrainment masks: Jet mixing is how they work; The Bernoulli and Venturi Principles are How They Don't", Respiratory Care 1979, vol. 24, No. 10 (4 pages).
Spence, et al, "Development of a High-Flow Nasal Cannula and Pharmaceutical Aerosol Combination Device", J Aerosol Med Pulm Drug Deliv. Mar. 21, 2019. doi: 10.1089/jamp.2018.1488. [Epub ahead of print] PMID: 30855199.

* cited by examiner

HEATED NEBULIZER ADAPTER FOR RESPIRATORY THERAPY

CROSS REFERENCE TO RELATED APPLICATIONS

This application claims the benefit of U.S. Provisional Application No. 62/008,880, filed on Jun. 6, 2014, which is hereby incorporated herein by reference in its entirety.

BACKGROUND

Patients with respiratory ailments may be treated with respiratory assist devices, for example devices that deliver supplemental breathing gas to a patient. Such devices include devices that deliver gas to a patient using high flow therapy (HFT). HFT devices deliver a high flow rate of breathing gas to a patient via a nasal cannula to increase a patient's fraction of inspired oxygen (FiO2) while decreasing a patient's work of breathing. Some HFT devices heat and humidify the delivered breathing gas to reduce patient discomfort.

Patients receiving respiratory therapy may also benefit from administration of nebulized medications. Nebulizers allow aerosolized respiratory medications, such as bronchodilators (e.g., Albuterol (Ventolin), Salbutamol (Proventil), Levosalbutamol/Levalbuterol (Xopenex)) for treating asthma or Chronic Obstructive Pulmonary Disease (COPD) to be administered through inhalation directly to a patient's lungs. Nebulizers may be connected to respiratory assist devices to supply nebulized medication together with supplemental breathing gas. Such systems can allow a patient to receive the medication without stopping use of a respiratory assist device.

A combination of nebulized medication and HFT can be used to assist patients experiencing respiratory distress and provide a comfortable and effective management of cardiopulmonary conditions. A challenge associated with delivering nebulized medication via a high-flow system is condensation of moisture from the mixture of heated and humidified breathing gas and nebulized medication. Condensation in a ventilation circuit presents both clinical and mechanical challenges, as the condensate can build up to limit flow through the system and also collect and stagnate which presents a biologic hazard to the patient.

SUMMARY

Disclosed herein are systems, devices, and methods for heating nebulizer adapters used in respiratory therapy. In certain implementations, the systems, devices, and methods include a nebulizer adapter with a gas mixing chamber surrounded by a fluid cavity. Nebulized medication is mixed with heated and humidified breathing gas in the gas mixing chamber. Heating fluid is passed into the fluid cavity to heat the gas mixing chamber, thereby reducing condensation of moisture from the heated and humidified breathing gas. Condensate that does collect in the gas mixing chamber is drained through a drain port. The drain port may pass the condensate into an evaporative dispersal system, a condensate trap, an absorbent pad, or any other suitable moisture removing device. These systems devices and methods provide an effective method for reducing unwanted condensation in the ventilation circuit and for managing condensation that does occur, thereby enabling continuous or semi-continuous operation of high flow therapy (HFT) with nebulized medication. Furthermore, by locating the fluid cavity in the nebulizer adapter rather than in the nebulizer itself, a simpler nebulizer may be used which may facilitate the use of single-dose nebulizers.

The nebulizer adapter disclosed herein can be used with a wide range of nebulizers, including vibrating mesh nebulizers (e.g., the AERONEB® nebulizer), ultrasonic nebulizers (e.g., nebulizers with a vibrating piezocrystal), nebulizers using compressed gases, jet nebulizers, single-dose nebulizers, or reusable nebulizers. In a preferred embodiment, the nebulizer adapter is used with HFT, but the nebulizer adapter may also be used with other types of respiratory therapy and respiratory therapy devices, including low flow oxygen therapy, continuous positive airway pressure therapy (CPAP), mechanical ventilation, oxygen masks, Venturi masks, and tracheotomy masks.

In one aspect, a nebulizer adapter includes a cup having an interior wall defining a gas mixing chamber, an exterior wall, and a fluid cavity disposed between the interior wall and the exterior wall. The nebulizer adapter also includes an inlet port having a fluid lumen in fluid communication with the fluid cavity and a breathing gas inlet lumen in fluid communication with the mixing chamber, an outlet having a breathing gas outlet lumen, and a drain port in fluid communication with the mixing chamber and having a drain lumen that passes from the interior wall to the exterior wall of the cup. In certain implementations, the fluid lumen is concentric with the breathing gas inlet lumen.

In certain implementations, the drain port is in fluid communication with an evaporative dispersal system. The evaporative dispersal system may include a frame, a wicking layer covering the frame, and a semipermeable bacteriostatic layer covering the wicking material. In certain implementations, a delivery tube is connected to the inlet port and the evaporative dispersal system is supported on an outer surface of the delivery tube along a length of the delivery tube configured to wick condensate from a first region proximal to the drain port towards a second region distal to the drain port. The wicking layer may be a water-insoluble biocompatible material. In certain implementations the wicking layer is a hydrocarbon.

In certain implementations, the drain port is in fluid communication with a condensation trap. The drain port may be connected to a glass filter having an average pore diameter less than 0.5 microns and the glass filter is connected to an absorbent pad.

In certain implementations, the nebulizer adapter includes a plug configured to substantially occlude the mixing chamber when the nebulizer is not attached to the cup. Alternatively, the nebulizer adapter may include an inflatable balloon configured to substantially occlude the mixing chamber when the nebulizer is not attached to the cup.

In certain implementations, the fluid lumen of the inlet port comprises a divider for separating an inflow passage for carrying fluid to the cup and an outflow passage for carrying fluid away from the cup. The outlet port may be configured to connect to a nasal cannula. In certain implementations, the outflow port includes an outflow fluid lumen in fluid communication with the fluid cavity and an outflow breathing gas lumen in fluid communication with the mixing chamber. The outflow fluid lumen may be concentric with the outflow breathing gas lumen.

In another aspect, a method for delivering aerosolized medication combined with heated and humidified breathing gas includes coupling a nebulizer containing a medication to a nebulizer adapter having a mixing chamber and a fluid cavity surrounding the mixing chamber, passing a heated fluid through the fluid cavity of the nebulizer adapter to heat the mixing chamber, nebulizing the medication and transmitting the nebulized medication into the mixing chamber, passing a heated and humidified breathing gas through the mixing chamber and out an outlet port, and passing a condensate from the mixing chamber through a drain port. In certain implementations, the method of further includes passing the condensate into an evaporative dispersal system. In certain implementations, the method further comprises passing the condensate into a condensate trap. In certain implementations, the method further includes passing the condensate through a glass filter into an absorbent pad.

In certain implementations, the method further includes removing the nebulizer from the nebulizer adapter, and inserting a plug into the nebulizer adapter to fill most of the mixing chamber. In certain implementations, the method further includes removing the nebulizer from the nebulizer adapter, and inflating a balloon to fill most of the mixing chamber. In certain implementations, the method further includes circulating the fluid in the fluid cavity. The method may further include connecting the outlet port to a nasal cannula.

In another aspect, a nebulizer adapter includes means for releasably receiving a nebulizer and having mixing means for mixing a heated and humidified breathing gas with a nebulized medication and heating means for heating the mixing means using a fluid, means for delivering a fluid to the heating means, means for delivering heated and humidified breathing gas to the mixing means, means for passing a mixed gas out of the mixing means, and means for draining condensate from the mixing means. In certain implementations, the means for fluidly connecting the fluid to the heating means is concentric with the means for delivering heated and humidified breathing gas to the mixing means.

In certain implementations, the nebulizer adapter further includes means for passing the condensate into an evaporative dispersal system. The nebulizer adapter may further include means for passing the condensate into a condensate trap. The nebulizer adapter may further include means for passing the condensate through a glass filter into an absorbent pad. The nebulizer adapter may further include means for plugging the nebulizer adapter to fill most of the mixing chamber.

In certain implementations, the nebulizer adapter further includes means for inflating a balloon to fill most of the mixing chamber. In certain implementations, the nebulizer adapter further includes means for circulating the fluid in the fluid cavity. In certain implementations, the nebulizer adapter further includes means for connecting a nasal cannula to the means for passing a mixed gas out of the mixing means.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
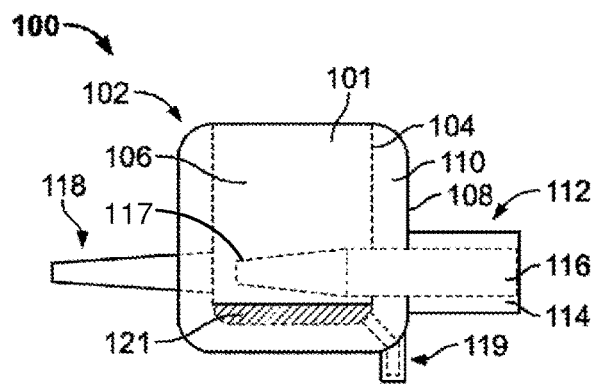
FIG. 1 shows an illustrative nebulizer adapter.

To provide an overall understanding of the systems, devices, and methods described herein, certain illustrative embodiments will be described. Although the embodiments and features described herein are specifically described for use in connection with a high flow therapy system, it will be understood that all the components and other features outlined below may be combined with one another in any suitable manner and may be adapted and applied to other types of respiratory therapy and respiratory therapy devices, including low flow oxygen therapy, continuous positive airway pressure therapy (CPAP), mechanical ventilation, oxygen masks, Venturi masks, and tracheotomy masks.

The systems, devices and methods described herein provide a nebulizer adapter that allows simultaneous administration of nebulized drugs and respiratory therapy. The nebulizer adapter addresses potential complications caused by condensation in the ventilation circuit by reducing risk of condensation and providing devices that remove condensate that does collect during therapy. The nebulizer adapter reduces the rate of condensation by reducing cooling due to heat loss to the ambient environment and by reducing cooling due to gas expansion when breathing gas enters a mixing chamber of the adapter in which heated and humidified breathing gas is mixed with nebulized medication. In particular, the nebulizer adapter reduces heat loss from the mixing chamber by circulating a heating fluid through a fluid cavity surrounding the mixing chamber. To reduce cooling due to gas expansion when a nebulizer is not coupled to the nebulizer adapter, the nebulizer adapter is configured to receive a plug that reduces the available volume of the mixing chamber. In addition to reducing the rate of condensation, the nebulizer adapter also manages condensate that does collect through use of one or more moisture removal systems including evaporative dispersal systems, absorbent pads, or condensate traps.

The design of the nebulizer adapter also facilitates the use of single-dose nebulizers. Single-dose nebulizers reduce the risk of contaminating the ventilation circuit compared to reusable nebulizers. Because the mixing chamber is heated by a fluid cavity in the nebulizer adapter instead of in the nebulizer itself, modifications to the nebulizer are not required for use with the present system. This reduces the number of parts needed to incorporate the nebulizer, and when the nebulizer is removed and replaced, a heating fluid connection does not have to be disconnected from the nebulizer. Instead, the heating fluid remains continuously connected to the nebulizer adapter. This design allows heating fluid to be continuously circulated and reduces the risk of spilling or contaminating heating fluid in the circuit.

The design of the nebulizer adapter also provides connection to a multi-lumen ventilation circuit. For instance, if the ventilation circuit carries both breathing gas and heating fluid in a single delivery tube with multiple lumens, that delivery tube may be connected to the nebulizer adapter at a single point. This single connection point reduces the bulk of the connection between the adapter and the ventilation circuit by reducing the number of connections and tubing adapters needed compared to an adapter or nebulizer having separate ports for breathing gas and heating connections.

FIG. 1 shows a nebulizer adapter for use in a respiratory therapy circuit. The nebulizer adapter 100 includes a cup 102 configured to receive a nebulizer through an opening 101 of the adapter. The cup 102 has an interior wall 104 that defines a gas mixing chamber 106 and an exterior wall 108. A fluid cavity 110 is disposed between the interior wall 104 and the exterior wall 108. A heating fluid is delivered to and circulated in the fluid cavity 110 to heat the gas mixing chamber 106.

The nebulizer adapter 100 also includes an inlet port 112 connected to the cup 102. The inlet port 112 has a fluid lumen 114 and a breathing gas lumen 116. The fluid lumen 114 is in fluid communication with the fluid cavity 110 and enables a heating fluid to be delivered to the fluid cavity 110. The breathing gas lumen 116 is in fluid communication with the mixing chamber 106 and allows breathing gas to be delivered to the gas mixing chamber 106. The breathing gas may be a heated and humidified gas and have high oxygen content. In certain embodiments, breathing gas is passed into the breathing gas lumen at a rate of between eight and forty liters per minute, though any suitable flow rate may be used for a particular therapy or application. The breathing gas lumen 116 is concentric with the fluid lumen 114, and thus both heating fluid and breathing gas can be delivered to the nebulizer adapter from a delivery tube at a single connection point. Having a single point of connection to a single delivery tube allows for simpler and more compact attachment (e.g., fewer tubes and connectors) compared to systems with separate delivery tubes for breathing gas and heating fluid.

The nebulizer adapter 100 also includes an outlet 118 and a drain port 119, both of which are in fluid communication with the gas mixing chamber 106. The outlet 118 passes breathing gas that has been mixed with nebulized medication from the mixing chamber 106. The nebulizer adapter 100 may be located proximate to the patient, in which case the outlet port 118 may be connected to a nasal cannula, or the nebulizer adapter may be located proximate to the source of heated and humidified breathing gas. In such a configuration, the gas exiting the gas mixing chamber 106 through outlet 118 may be connected to a delivery tube carrying a heated fluid to reduce condensation as discussed below in relation to FIG. 8.

The drain port 119 on nebulizer adapter 100 removes condensate from the mixing chamber 106. Condensate can form in the mixing chamber 106 due to cooling of the heated and humidified breathing gas. Condensation is a particular concern for HFT because HFT devices supply breathing gas with a high relative humidity and a high temperature. If condensate is not managed, it can flood a patient's nasal passages or collect and stagnate in the ventilation circuit which presents a biologic hazard to the patient. The collection of condensation can prevent continuous use of therapy, because therapy may be interrupted periodically for removal of condensate. To address these challenges, the nebulizer adapter 100 continuously eliminates condensate through the drain port 119. The drain port 119 is located at the bottom of the cup 102 such that gravity draws the condensate to the drain port 119. Pressure in the gas mixing chamber 106 also forces the condensate through drain port 119. Drain port 119 may pass condensate to an evaporative dispersal system, an absorbent pad, a condensate trap or another suitable device to remove moisture. The drain port 119 may be a small aperture to reduce the risk of substantial loss of breathing gas flow. A small aperture also reduces the risk of introduction of outside contaminants through the drain port 119 into the mixing chamber 106.

While FIG. 1 shows the nebulizer adapter without a nebulizer, in use a nebulizer is inserted into cup 102 as shown in FIG. 2. FIG. 2 shows the nebulizer adapter 100 of FIG. 1 coupled to a nebulizer 120. The nebulizer 120 slides through opening 101 into the gas mixing chamber 106 defined by interior wall 104. The outer wall of nebulizer 120 engages in an interference fit with interior wall 104. The nebulizer 120 may be a vibrating mesh nebulizer, an ultrasonic nebulizer (e.g., a nebulizer with a vibrating piezocrystal), a jet nebulizer, or any other suitable type of nebulizer. Also, the nebulizer 120 may be a single-dose nebulizer or a reusable nebulizer. The nebulizer 120 dispenses nebulized medication into mixing chamber 106 through one or more openings on bottom face 122 of the nebulizer 120. As used herein, the term nebulized is understood to also include aerosolized or atomized medication. Nebulized medications may include a respiratory medication, such as a bronchodilator.

The nebulized medication mixes with heated and humidified breathing gas that is passed into the mixing chamber through a nozzle 117, and the breathing gas mixed with nebulized medication is then passed out of outlet 118. When the heated and humidified gas is introduced into mixing chamber 106, condensation may occur due to cooling. The condensation is undesirable because condensate could limit the gas flow through the system, present a biologic hazard to the patient, or could potentially flow into a nasal cannula and enter a patient's nasal passage. Condensation is a particular concern for HFT because HFT devices supply breathing gas at a high flow rate. When the breathing gas is pre-heated and humidified for patient comfort, HFT provides a high flow of gas with a high relative humidity and a high temperature. The heating and humidifying of the breathing gas used in HFT is beneficial because high flow rates of dry breathing gas leads to patient discomfort (e.g., due to drying of nasal passages). When heated and humidified gas cools, some of the moisture carried in the breathing gas cannot remain soluble and condenses. With the high flow rate of HFT, there is a substantial amount of moisture in the breathing circuit that could potentially become condensate if the gas cools. Cooling of the heated and humidified gas can occur due to expansion of the gas as it exits nozzle 117 and enters the gas mixing chamber 106. Cooling can also occur due to heat loss to the ambient environment (e.g., radiative cooling at the plastic walls of the adapter).

The circulation of heated fluid in fluid cavity 110 reduces the cooling relative to an uninsulated nebulizer adapter. In certain embodiments, the heating fluid entering the fluid cavity has a temperature of about 43 degrees Celsius and the breathing gas entering the mixing chamber may have a temperature of about 35 to 43 degrees. In such embodiments, the breathing gas is insulated and heated by the heating fluid to counteract cooling due to gas expansion. The circulation of the heating fluid increases the convective heat transfer rate between the gas mixing chamber 106 and the fluid in the fluid cavity 110 relative to still water. Circulation of the heating fluid also allows the fluid to continuously deliver heat to the gas in the mixing chamber 106 while being continuously reheated at a heating unit (not shown) elsewhere in the circuit. The decreased cooling of the breathing gas due to the heating fluid reduces the rate of condensation in mixing chamber 106.

Figure 3:
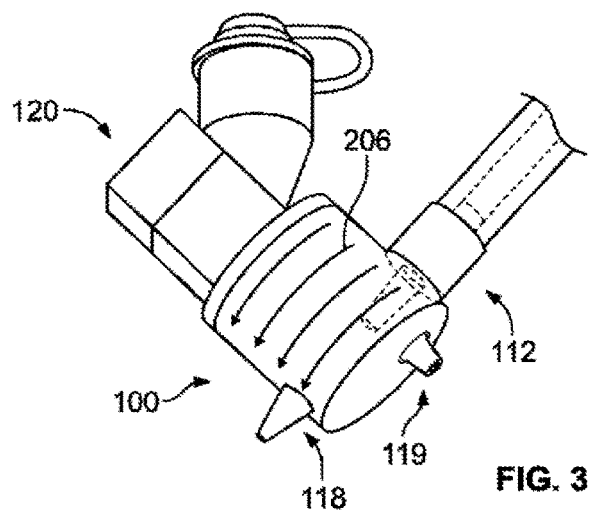
FIG. 3 shows the nebulizer adapter of FIG. 1 with heating fluid circulating in the adapter.
Figure 4:
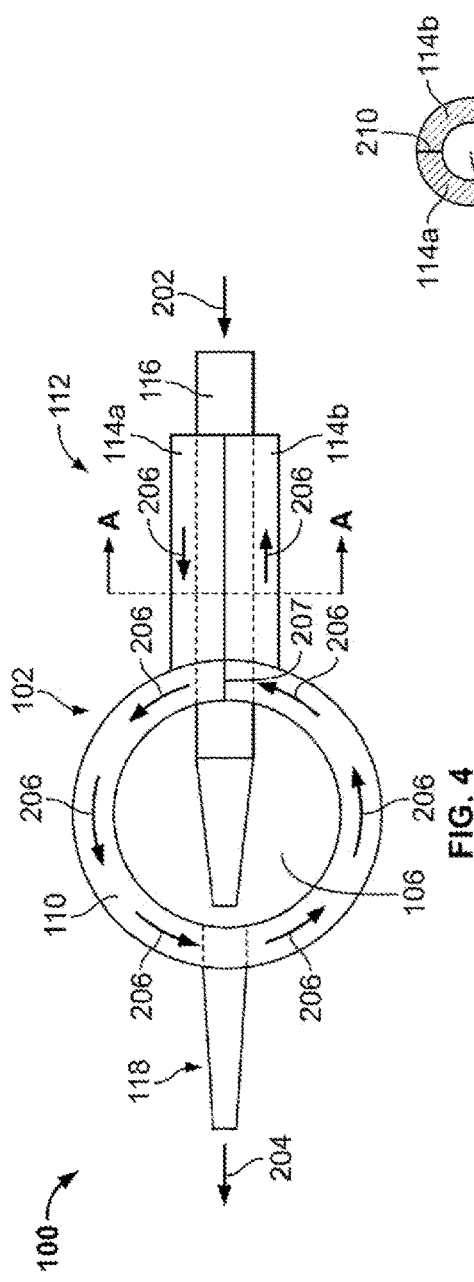
FIG. 4 shows a top view of the nebulizer adapter of FIG. 1 with heating fluid circulating in the adapter.

A perspective view of the nebulizer adapter 100 of FIG. 1 with arrows 206 showing the path of the circulating heating fluid is shown in FIG. 3. FIG. 4 shows a corresponding top view with the nebulizer 120 removed to show another view of the path of fluid flow through the fluid cavity 110. The direction of circulation of heating fluid in both figures is indicated by arrows 206, and the direction of the flow of breathing gas is shown by arrows 202 and 204.

Referring to FIG. 4, the inlet port 112 has three passages for fluid and gas: a fluid inflow passage 114a, a fluid outflow passage 114b, and a breathing gas lumen 116. The use of two fluid passages allows heating fluid to pass into and out of the fluid cavity 110, while the additional gas lumen allows for separate transport of heated and humidified breathing gas. Heating fluid enters fluid inflow passage 114a and provides thermal insulation within 110 before returning through fluid outflow passage 114b. Internal walls of the fluid cavity 110 direct the heated fluid from fluid inflow passage 114a, around the periphery of the fluid cavity 110, before exiting through the fluid outflow passage 114b. Thus, the circulation of the heating fluid allows heat to be continuously supplied to fluid cavity 110. In certain embodiments, heated fluid flows in a closed circuit so that the heating fluid is continuously recycled and reheated as necessary by a high flow therapy unit (not shown). The fluid circulating within fluid cavity 110, in turn, insulates the breathing gas and nebulized medication in the gas mixing chamber. After mixing, the breathing gas mixed with nebulized medication exits outlet 118.

Figure 5:
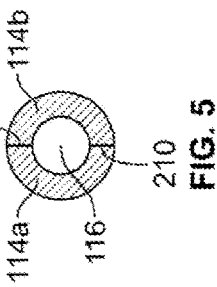
FIG. 5 shows a cross section taken along section line A-A of the nebulizer adapter in FIG. 5.

FIG. 5 shows a cross section taken along section line A-A of the nebulizer adapter of FIG. 4. The cross-section shows that the breathing gas lumen 116 is concentric with a fluid lumen defined by the fluid inflow passage 114a and the fluid outflow passage 114b, which are separated by divider 210. By surrounding the breathing gas lumen 116 with the heated fluid, the breathing gas is insulated from ambient air and maintained at a temperature above the ambient temperature, thus reducing condensation. As discussed above, the concentric fluid lumen and breathing gas lumen may simplify connection to delivery tubing by minimizing the number of separate attachment points.

Figure 6:
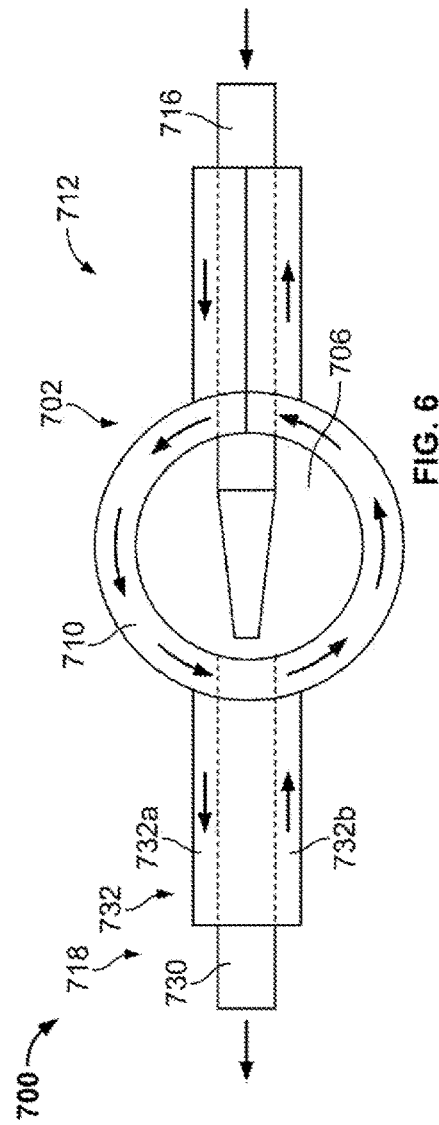
FIG. 6 shows a top view of an illustrative nebulizer adapter with heating fluid circulating in the adapter.

While the nebulizer adapter in FIG. 4. shows a single lumen outlet 118, the adapter outlet may have two or more output lumens to pass both breathing gas and heating fluid downstream in the ventilation circuit. FIG. 6 shows a top view of a nebulizer adapter 700 with the nebulizer removed to show the path of fluid flow through the fluid cavity 710. The outlet 718 of the nebulizer adapter 700 has two lumens, an outflow fluid lumen 732 and an outflow gas lumen 730. The outflow fluid lumen 732 is in fluid communication with fluid cavity 710, and the outflow gas lumen 730 is in fluid communication with the gas mixing chamber 706. By providing a fluid lumen 732 on the outlet, heating fluid that is passed into fluid cavity 710 can be further passed into tubing that carries the breathing gas mixed with nebulized medication out of the mixing chamber 706. The outflow fluid lumen 732 surrounds the outflow gas lumen 730, and the heating fluid passed through the outflow fluid lumen 732 insulates and warms the breathing gas exiting the mixing chamber 706. The outflow fluid lumen 732 may be divided into two passages, a first passage 732a carrying heating fluid exiting fluid cavity 710 and a second passage 732b carrying heating fluid returning to fluid cavity 710. The insulation and heat provided by the heating fluid in the outflow fluid lumen 732 reduces condensation of moisture in the breathing gas on its way to the patient. Such a configuration may be desirable in instances where the nebulizer is located in a breathing circuit and away from the patient (e.g., when the nebulizer adapter is proximate to the source of the heated and humidified breathing gas).

Figure 7:
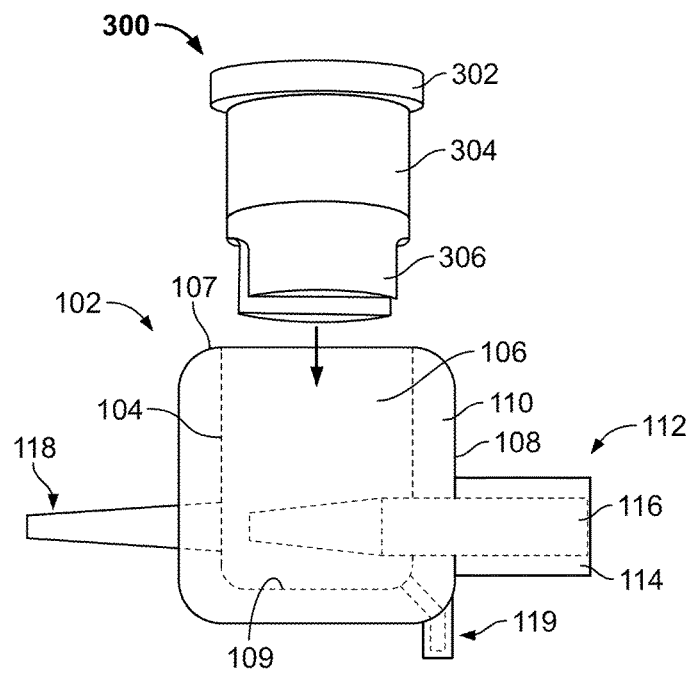
FIG. 7 shows the illustrative nebulizer adapter of FIG. 1 coupled to a volume filling plug.

While heating the mixing chamber as discussed above reduces cooling of the breathing gas due to heat loss to the ambient environment, cooling due to gas expansion can also be reduced by reducing the available volume of mixing chamber 106 when a nebulizer is not being used. FIG. 7 shows the nebulizer adapter of FIG. 1 with a volume filling plug 300 aligned to be inserted into mixing chamber 106 in place of a nebulizer. The volume-filling plug 300 has a cylindrical body 304 that mates with interior wall 104. The cylindrical body 304 may form an interference fit with interior wall 104 that serves to hold the volume-filling plug firmly in position, while also sealing the mixing chamber 106 to prevent the escape of breathing gas. Insertion of the plug 300 into the mixing chamber 106 is limited by a flange 302 which makes contact with the upper surface 107 of the cup 102. The flange 302 may also form a seal with the upper surface 107 of the cup 102 to reduce the risk of gas leaking out of the mixing chamber 106. Alternatively, the volume-filling plug 300 may be inserted into the mixing chamber 106 until the bottom surface of plug 306 engages the bottom surface 109 of interior wall 104. The volume-filling plug 300 has a protrusion 306 which mates with nozzle 117 so that when the volume-filling plug 300 is fully inserted into the mixing chamber 106, the protrusion 306 extends over both sides of nozzle 117. The mating fit thus reduces the expansion of the breathing gas that passes through the adapter, while not blocking the flow of that breathing gas. In certain embodiments, a balloon is used in place of the volume-filling plug. For example, a balloon may be built into the cup 102 and inflated with saline or air when the nebulizer 120 is not inserted. Such a balloon may subsequently be deflated before reinsertion of the nebulizer 120.

Figure 8:
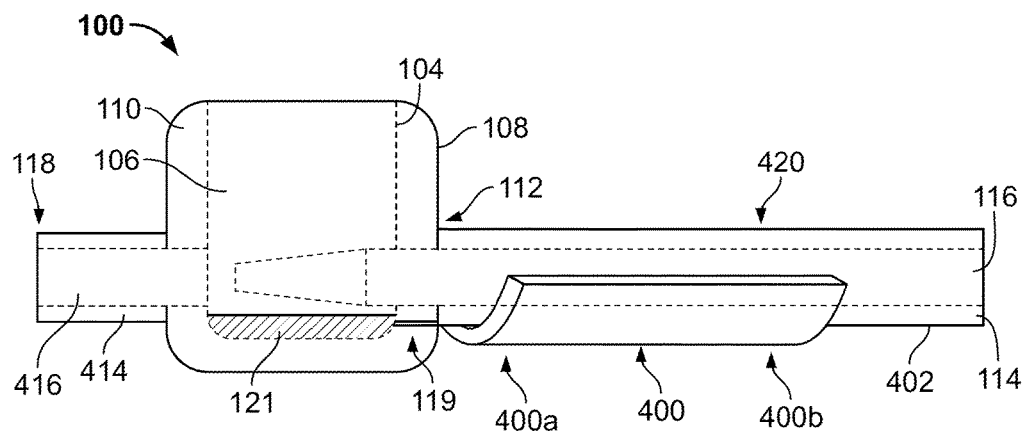
FIG. 8 shows the nebulizer adapter of FIG. 1 with an evaporative dispersal system.

Reducing cooling due to gas expansion as described above reduces the rate of condensation of moisture from the breathing gas, but some condensation may still occur in mixing chamber 106 during use. It is desirable to remove condensate that collects in cup 102 for patient safety. One possible means for removal of that condensate is evaporative dispersal. FIG. 8 shows the nebulizer adapter 100 of FIG. 1 coupled with an evaporative dispersal system according to certain embodiments. Although the evaporative dispersal system 400 is shown on a nebulizer adapter that has an outflow fluid lumen at its outlet, it may also be preferable to use the evaporative dispersal system 400 in embodiments in which the nebulizer adapter is proximal to the patient. The evaporative dispersal system 400 is connected to the drain port 119 of nebulizer adapter 100. The connection to drain port 119 can be permanent and may be held using an adhesive, ultrasonic weld, or another suitable permanent attachment mechanism. Alternatively, the connection to drain port 119 may be temporary and may be held by a positive attachment mechanism (e.g., a Luer lock) or an interference fit. The evaporative dispersal system 400 is mounted on delivery tubing 420 which is connected to the inlet port 112. Condensate 121 that collects in cup 102 may be forced by gas pressure in mixing chamber 106 to flow through drain port 119 into the evaporative dispersal system. The condensate may be driven by capillary action from a region 400a proximal to the drain port 119 towards a region 400b distal to the drain port 119. As the condensate is wicked along the length of evaporative dispersal system 400, it also evaporates into ambient air.

Figure 9:
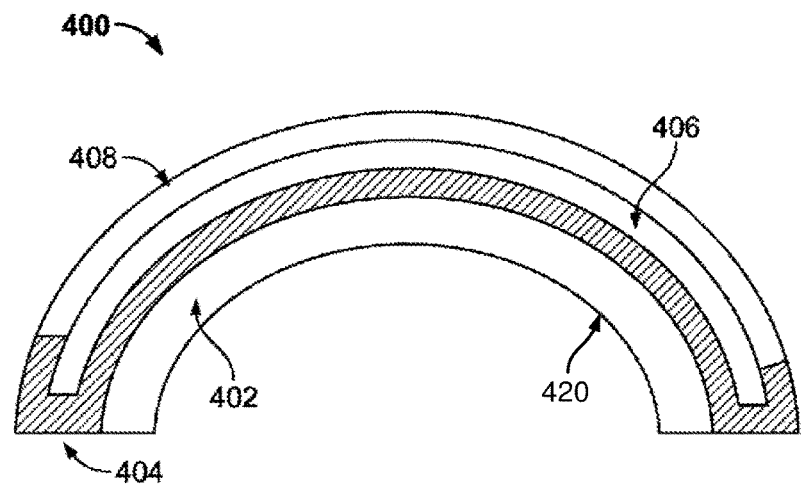
FIG. 9 shows a cross section of the evaporative dispersal system of FIG. 8.

A cross section of the evaporative dispersal system 400 is shown in FIG. 9. The evaporative dispersal system is supported by the wall 402 of the delivery tubing 420 and includes a frame 404, a wicking layer 406 covering the frame 404, and a semi-permeable bacteriostatic layer 408 covering the wicking material 406. The frame 404 may be fused to the delivery tube 420 or bonded temporarily. The semi-permeable bacteriostatic layer 408 is affixed to the plastic frame 404. The gap between the inner surface of the semi-permeable bacteriostatic layer 408 and the outer surface of the plastic frame is filled with the wicking material 406. The wicking material 406 promotes the mobilization of condensate down the length of the evaporative device. The wicking material 406 may be biocompatible and water insoluble. In certain embodiments, the wicking material is a hydrocarbon. A hydrocarbon wicking material may allow diffusion of the condensate while prohibiting significant microbiological contamination from reentering the closed system.

Figure 10:
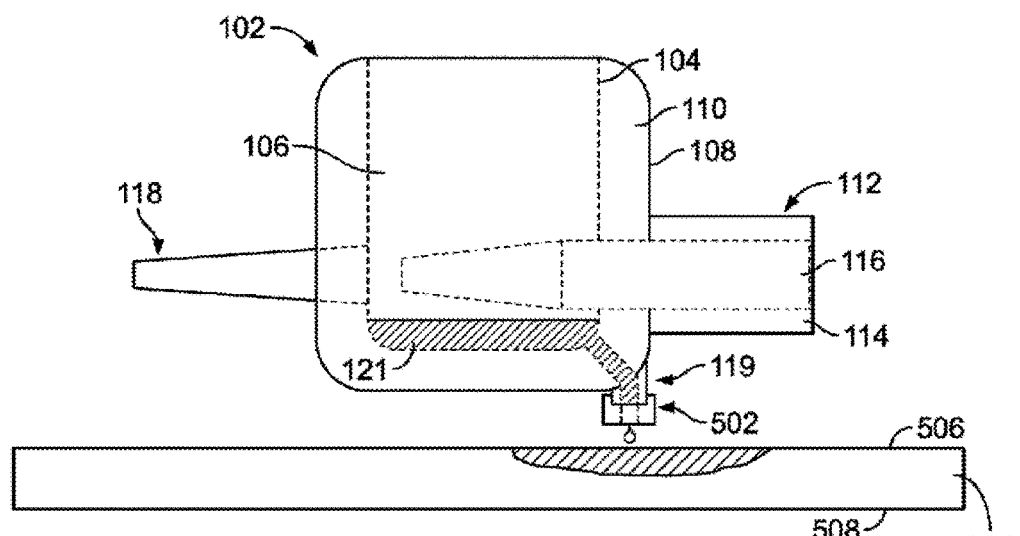
FIG. 10 shows the nebulizer adapter of FIG. 1 and an absorbent pad.

While an evaporative dispersal system may be used to remove condensate from the nebulizer adapter, an absorbent pad may also be used for removal of condensate. FIG. 10 shows the nebulizer adapter 100 of FIG. 1 placed over an absorbent pad 504. For simplicity, neither the nebulizer adapter nor the volume-filling plug is shown inserted in cup 102. Condensate 121 that collects in gas mixing chamber 106 exits mixing chamber 106 through drain port 119 and is passed through a filter 502. The filter allows the condensate 121 to seep through and pass into the absorbent pad 504. In certain embodiments, the filter 502 is a glass filter with an average pore diameter pore of less than 0.5 µm. The glass filter allows smooth dispersal of the condensate while also keeping outside contaminants from entering the ventilation circuit through the drain port. Pressure inside the mixing chamber 106 can cause condensate exiting the chamber to spray, often with a whistling sound, out of the chamber. The glass filter provides for quiet dispersal of the condensate in a liquid state to be soaked up by the absorbent pad 504. The filter also serves as a contamination shield, reducing the risk of bacteria entering the mixing chamber 106. The absorbent pad 504 may be placed on a patient's chest such that the bottom surface 508 rests on the patient's chest, while the upper surface 506 is exposed so that condensate 121 exiting filter 502 may be absorbed.

Figure 11:
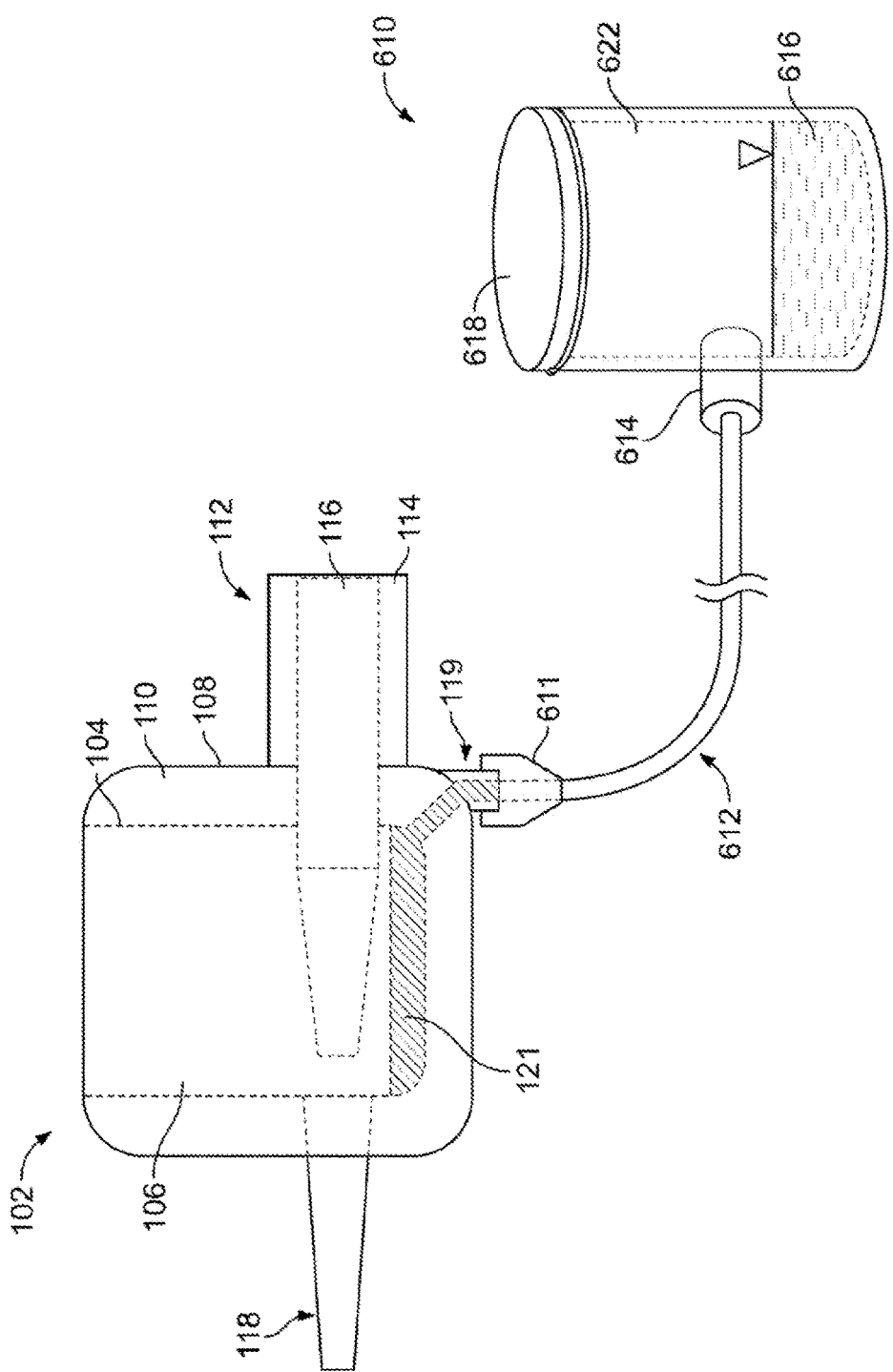
FIG. 11 shows the nebulizer adapter of FIG. 1 coupled with a condensate trap.

In certain applications, condensate can also be removed using a condensate trap. FIG. 11 shows the nebulizer adapter of FIG. 1 coupled with a condensate trap 610. Condensate trap 610 is connected to the drain port 119 on cup 102 via tubing 612. Flow of the condensate 121 into the tubing 612 may be facilitated by the positive pressure inside mixing chamber 106 relative to the pressure inside the condensate trap 610. A pressure differential between the mixing chamber 106 and the inside of the condensate trap 610 may be achieved due to a vented filter 618 on the condensate trap 610 which allows the pressure in the interior 622 of condensate trap 610 to be closer to atmosphere pressure. The filter material for the vented filter 618 may be hydrophobic to prevent the rapid outflow of trapped condensate 616 from the condensate trap 610.

The tubing 612 is connected to the condensate trap via connector 614, which may provide a permanent attachment or a reversible positive locking mechanism (e.g., Luer lock). A reversible positive locking mechanism may facilitate replacement of the condensate trap. In embodiments where a reversible positive locking mechanism is not used, the lid of the condensate trap 610 may be removable for emptying the condensate trap 610. Although the condensate trap 610 is depicted as about the same size as cup 102, in certain embodiments, condensate trap 610 has a capacity of 1 liter or more. In such embodiments, the condensate trap may be located on a stand included with the unit that supplies the heated and humidified breathing gas.

Figure 2:
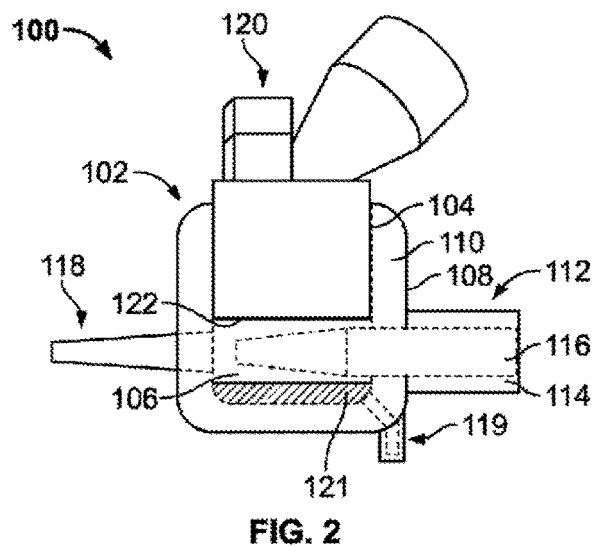
FIG. 2 shows the nebulizer adapter of FIG. 1 coupled to a nebulizer.
Figure 12:
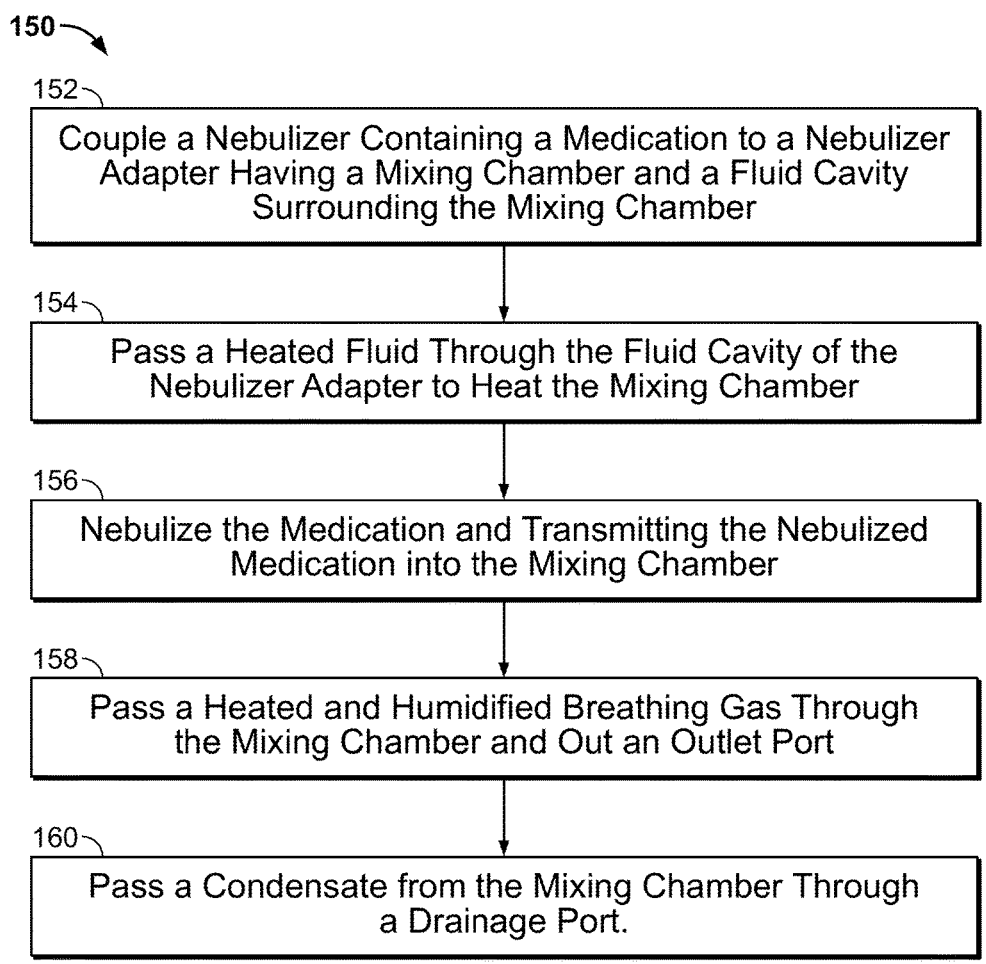
FIG. 12 shows an illustrative process for delivering aerosolized medication combined with heated and humidified breathing gas.
Figure 13:
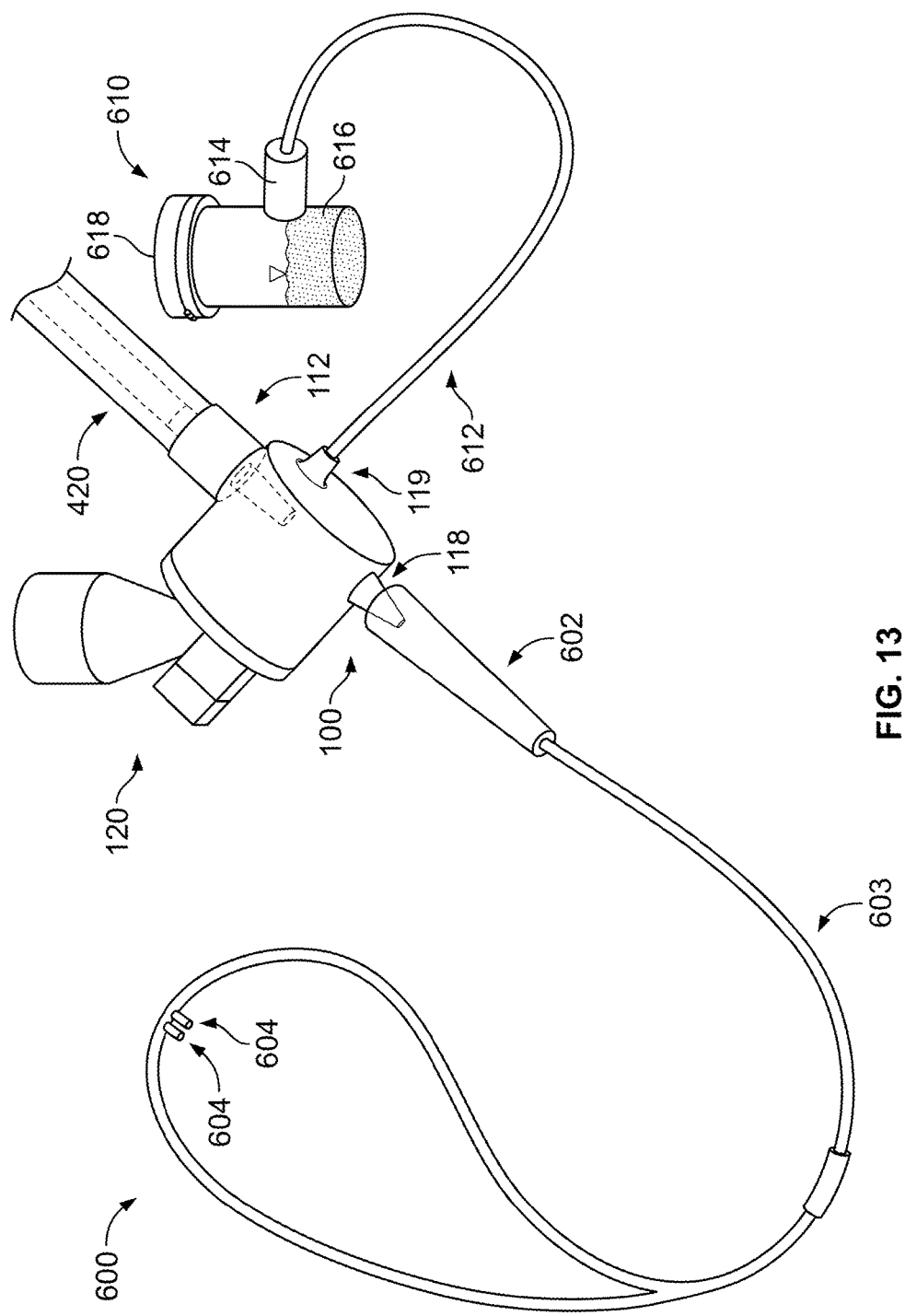
FIG. 13 shows the nebulizer adapter of FIG. 1 in line with a high flow therapy system.

The nebulizer adapter described above, or other adapters for incorporating nebulizers and heating fluid into a breathing circuit, may be used according to the process described in FIG. 12. FIG. 12 shows a method 150 for delivering aerosolized medication combined with heated and humidified breathing gas. The method outlined in flowchart 150 may be practiced using the nebulizer adapter 100 of FIGS. 1 and 2. It will be understood by one of ordinary skill in the art that, prior to the steps shown in FIG. 12, a heated and humidified breathing gas may be generated for delivery to a patient by any suitable means.

In step 152, a nebulizer containing a medication is coupled to a nebulizer adapter having a mixing chamber and a fluid cavity surrounding the mixing chamber. In step 154, a heating fluid is passed through the fluid cavity of the nebulizer adapter to heat the mixing chamber. Heating the mixing chamber can reduce cooling of the breathing gas in the mixing chamber that can lead to condensation of moisture from the breathing gas. In certain embodiments, the heating fluid entering the fluid cavity has a temperature of about 43 degrees Celsius which is at or above the temperature of the breathing gas in the mixing chamber to facilitate heating of the breathing gas.

In step 156, the medication is nebulized and transmitted into the mixing chamber 106. In step 158, a heated and humidified breathing gas is passed through the mixing chamber to entrain the nebulized medication in the flow of breathing gas. The breathing gas mixed with nebulized medication is passed out of an outlet port after mixing. In some embodiments, the breathing gas has a temperature of about 35 to 43 degrees upon exiting the mixing chamber. Moisture from the heated and humidified breathing gas may condense in step 158 due to cooling effects such as expansive cooling and heat loss to the ambient environment. These cooling effects are mitigated by the heat and insulation provided by the heating fluid in the fluid cavity. If condensate forms despite the heating, the condensate is passed from the mixing chamber through a drain port in step 160. In certain embodiments, the condensate is passed through the drain port to an evaporative dispersal system, a condensate trap, an absorbent pad, or any other suitable moisture removing device. When the nebulizer is no longer needed or after the single-dose of a single-dose nebulizer has been delivered, the nebulizer may be removed and a volume filling plug inserted. The volume filing plug reduces the expansion of the breathing gas as it passes through the mixing chamber and thus may reduce cooling associated with gas expansion. The reduction in cooling can lead to a reduction in condensation.

The procedure and nebulizer adapters described above may be implemented with the high flow therapy (HFT) system shown in FIG. 13. FIG. 13 shows the nebulizer adapter of FIG. 1 in line with an HFT system according to certain embodiments. The nebulizer adapter 100 is connected to delivery tubing 420, water trap 610, nasal cannula 600, and nebulizer 120. The delivery tubing 420 connects to the inlet port 112 of the nebulizer adaptor 100. The other end of delivery tubing 420 is connected to a source of high flow heated and humidified breathing gas (not shown). The delivery tubing 420 delivers both heating fluid and heated and humidified breathing gas through at least two separate lumens. The heating fluid delivered by delivery tubing 420 enters the fluid cavity in nebulizer adapter 100, while the heated and humidified breathing gas enters the gas mixing chamber.

The nasal cannula 600 is connected to the outlet 118 of the nebulizer adapter 100 via connector 602 so that the interior of tubing 603 is in fluid communication with the gas mixing chamber inside nebulizer adapter 100. Heated and humidified gas mixed with nebulized medication exits outlet 118, travels through tubing 603, and exits out of opening 604 in the nasal cannula 600. The cannula 600 is sized for use with infants, but any other suitable nasal cannula may be used. When the nasal cannula 600 is worn by a patient, openings 604 may be inserted into the patient's nostrils so that the heated and humidified breathing gas mixed with nebulized medication may be injected into a patient's nasal passages.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in high flow therapy systems, may be applied to systems, devices, and methods to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. A nebulizer adapter comprising:

a cup having an interior wall defining a gas mixing chamber, an exterior wall, and a fluid cavity disposed between the interior wall and the exterior wall, the cup configured to releasably receive a nebulizer;

an inlet port having a fluid lumen in fluid communication with the fluid cavity and a breathing gas inlet lumen in fluid communication with the mixing chamber;

an outlet having a breathing gas outlet lumen; and a drain port in fluid communication with the mixing chamber and having a drain lumen that passes from the interior wall to the exterior wall of the cup.

2. The nebulizer adapter of claim 1, wherein the fluid lumen is concentric with the breathing gas inlet lumen.

3. The nebulizer adapter of claim 1, wherein the drain port is in fluid communication with an evaporative dispersal system.

4. The nebulizer adapter of claim 3, wherein the evaporative dispersal system comprises a frame, a wicking layer covering the frame, and a semipermeable bacteriostatic layer covering the wicking layer.

5. The nebulizer adapter of claim 4, wherein the wicking layer is a water-insoluble biocompatible material.

6. The nebulizer adapter of claim 4, wherein the wicking layer is a hydrocarbon.

7. The nebulizer adapter of claim 3, wherein a delivery tube is connected to the inlet port and the evaporative dispersal system is supported on an outer surface of the delivery tube along a length of the delivery tube configured to wick condensate from a first region proximal to the drain port towards a second region distal to the drain port.

8. The nebulizer adapter of claim 1, wherein the drain port is in fluid communication with a condensation trap.

9. The nebulizer adapter of claim 1, wherein the drain port is connected to a glass filter having an average pore diameter less than 0.5 microns and the glass filter is connected to an absorbent pad.

10. The nebulizer adapter of claim 1, further comprising a plug configured to substantially occlude the gas mixing chamber when the nebulizer is not received in the cup.

11. The nebulizer adapter of claim 1, further comprising an inflatable balloon configured to substantially occlude the mixing chamber when the nebulizer is not received in the cup.

12. The nebulizer adapter of claim 1, wherein the fluid lumen of the inlet port comprises a divider for separating an inflow passage for carrying fluid to the cup and an outflow passage for carrying fluid away from the cup.

13. The nebulizer adapter of claim 1, wherein the outlet port is configured to connect to a nasal cannula.

14. The nebulizer adapter of claim 1, wherein the outflow includes an outflow fluid lumen in fluid communication with the fluid cavity and an outflow breathing gas lumen in fluid communication with the mixing chamber.

15. The nebulizer adapter of claim 14, wherein the outflow fluid lumen is concentric with the outflow breathing gas lumen.

16. A method for delivering aerosolized medication combined with heated and humidified breathing gas, the method comprising:

coupling a nebulizer containing a medication to a nebulizer adapter having a mixing chamber and a fluid cavity surrounding the mixing chamber;

passing a heated fluid through the fluid cavity of the nebulizer adapter to heat the mixing chamber;

nebulizing the medication and transmitting the nebulized medication into the mixing chamber;

passing a heated and humidified breathing gas through the mixing chamber and out an outlet port; and passing a condensate from the mixing chamber through a drain port.

17. The method of claim 16, further comprising passing the condensate into an evaporative dispersal system.

18. The method of claim 16, further comprising passing the condensate into a condensate trap.

19. The method of claim 16, further comprising passing the condensate through a glass filter into an absorbent pad.

20. The method of claim 16, further comprising:

removing the nebulizer from the nebulizer adapter; and inserting a plug into the nebulizer adapter to fill most of the mixing chamber.

21. The method of claim 16, further comprising:

removing the nebulizer from the nebulizer adapter; and inflating a balloon to fill most of the mixing chamber.

22. The method of claim 16, further comprising circulating the fluid in the fluid cavity.

23. The method of claim 16, further comprising connecting the outlet port to a nasal cannula.

24. A nebulizer adapter comprising:

means for releasably receiving a nebulizer and having mixing means for mixing a heated and humidified breathing gas with a nebulized medication and heating means for heating the mixing means using a fluid;

means for delivering a fluid to the heating means;

means for delivering heated and humidified breathing gas to the mixing means;

means for passing a mixed gas out of the mixing means; and means for draining condensate from the mixing means.

25. The nebulizer adapter of claim 24, wherein the means for delivering the fluid to the heating means is concentric with the means for delivering heated and humidified breathing gas to the mixing means.

26. The nebulizer adapter of claim 24, wherein the means for draining condensate is fluidly connected to an evaporative dispersal system.

27. The nebulizer adapter of claim 24, wherein the means for draining condensate is fluidly connected to a condensate trap.

28. The nebulizer adapter of claim 24, wherein the means for draining condensate is fluidly connected to a glass filter configured to pass condensate into an absorbent pad.

29. The nebulizer adapter of claim 24, further comprising means for plugging the nebulizer adapter to fill most of the mixing means.

30. The nebulizer adapter of claim 24, further comprising an inflatable means configured to fill most of the mixing means.

31. The nebulizer adapter of claim 24, wherein the heating means comprises a heating fluid configured to circulate around the mixing means.

32. The nebulizer adapter of claim 24, further comprising means for connecting a nasal cannula to the means for passing a mixed gas out of the mixing means.

* * * * *